United States Patent [19]

Lorenz et al.

[11] 4,128,633

[45] Dec. 5, 1978

[54] PROCESS FOR PREPARING PVP-IODINE COMPLEX

[75] Inventors: Donald H. Lorenz, Basking Ridge, N.J.; Earl P. Williams, Pen Argyl, Pa.

[73] Assignee: GAF Corporation, New York, N.Y.

[21] Appl. No.: 791,520

[22] Filed: Apr. 27, 1977

[51] Int. Cl.$^2$ .................... A61K 31/79; A61K 33/18
[52] U.S. Cl. ....................................... 424/80; 424/150
[58] Field of Search ................................. 424/80, 150

[56] References Cited

U.S. PATENT DOCUMENTS

| | | | |
|---|---|---|---|
| 2,739,922 | 3/1956 | Shelanski | 424/150 |
| 2,900,305 | 8/1959 | Siggia | 424/150 |
| 3,898,326 | 8/1975 | Cantor et al. | 424/150 |
| 4,017,407 | 4/1977 | Cantor et al. | 424/150 |

*Primary Examiner*—Albert T. Meyers
*Assistant Examiner*—D. W. Robinson
*Attorney, Agent, or Firm*—Walter C. Kehm; Walter Katz

[57] ABSTRACT

In accordance with the present invention, there is provided herein an in situ process for making stable PVP-iodine complex having a high level of iodine power. The process of this invention is carried out by adding a predetermined amount of free water to a PVP suspension, and admixing iodine therewith to form the desired solid complex. The PVP suspension may be obtained by suspension polymerization of N-vinylpyrrolidone (VP) in a suitable solvent, and used directly for succeeding steps of the process.

5 Claims, No Drawings

PROCESS FOR PREPARING PVP-IODINE COMPLEX

BACKGROUND OF THE DISCLOSURE

1. Field of the Invention

This invention relates to a process for preparing a polyvinylpyrrolidone-iodine complex, generally called PVP-iodine, and, more particularly, it is concerned with an improved process which provides a stable complex for use as a germicidal and bactericidal composition.

2. Description of the Prior Art

PVP-iodine has been used extensively in hospitals and elsewhere for some time because of its germicidal, bactericidal, fungicidal and generally disinfecting properties. Usually it is sold as a brown powder, which contains about 10% available, or active iodine, and about 5% inactive iodine, in the form of the iodide ion.

The known processes for making commercial PVP-iodine are represented by such patents as U.S. Pat. Nos. 2,706,701, 2,739,922, 2,826,532, 2,900,305, 3,028,300, German Pat. No. 1,037,075 and German OL No. 2,439,197. These prior art processes are characterized by being deficient in one or more respects, particularly in that they are time-consuming and expensive, or require a large amount of iodine to produce a stable complex having an acceptable available iodine level.

Accordingly, it is an object of the present invention to provide an improved commercial process for making PVP-iodine by an economical method, which provides a high level of active iodine in the complex without requiring an excessive amount of iodine reactant, and which produces a stable composition of light coloration.

These and other objects and features of the invention will become apparent from the following more particular description of the invention.

SUMMARY OF THE INVENTION

In accordance with the present invention, there is provided herein an in situ process for making stable PVP-iodine complex having a high level of iodine power. The process of this invention is carried out by adding a predetermined amount of free water to a PVP suspension, and admixing iodine therewith to form the desired solid complex. The PVP suspension may be obtained by suspension polymerization of N-vinylpyrrolidone (VP) in a suitable solvent, and used directly for succeeding steps of the process.

DETAILED DESCRIPTION OF THE INVENTION

DESCRIPTION OF THE PREFERRED EMBODIMENTS

SUSPENSION POLYMERIZATION OF VP

In the first step of the preferred embodiment of the invention, vinylpyrrolidone is polymerized by a suspension polymerization technique to provide the PVP moiety of the desired PVP-iodine complex. The suspension polymerization is carried out by dissolving VP in a suitable solvent.

The solvents in the present suspension polymerization of vinylpyrrolidone are those in which vinylpyrrolidone is miscible and in which the vinylpyrrolidone polymeric product is substantially insoluble. The solvents are further characterized as being saturated aliphatic hydrocarbons. Illustrative of those solvents suitable for the present process are the saturated aliphatic hydrocarbons containing from 5 to about 20 carbon atoms which include mixtures of such compounds as may be prepared for such purpose or as may be found in commercially available mixtures such as for example, a petroleum cut of $C_6$–$C_{16}$ alkanes or other sources of hydrocarbon mixtures such as a kerosene or petroleum fraction boiling at about 175° C., e.g. Varsol; but above the temperature at which the polymerization effected. The preferred solvents for the present process are those alkanes having boiling points between 50° C. and 100° C. which are more easily separated from the polymeric product by boiling or evaporation. Most preferred of this group are normal and branched chain hexane, heptane, octane, and cycloalkanes such as, cyclopentane and cyclohexane. Solvent mixtures including even minor amounts of reactive oxygen-containing compounds, are best avoided in the present process since they tend to prematurely terminate polymer chains formed in the system and, in the case of certain azo initiators or catalysts, cause apparent deactivation which also materially limits the length of the polymer chains formed in the process by halting the reaction.

The amount of solvent needed for any suspension depends on several factors; namely, on the efficiency of agitation, the choice of catalyst, the temperature and pressure of operation and the optional use and amount of suspending agent present in the suspension medium. However generally, the solvent is employed in an amount equal to monomer up to a slight excess or as much as about 3.5 parts by weight per part by weight of monomer. The preferred amount of solvent employed in the present polymerization is between about 1.5 and about 2 parts by weight per part of monomer. Such a mixture provides an adequate dissipation of heat built up in the reaction zone by the formation of polymer in the beads or globules of the suspension while still maintaining the reaction volume at a reasonable level so as to avoid the need for oversized equipment and other inefficiencies and difficulties in product recovery. Generally, the amount of solvent employed is that necessary to maintain the suspension and avoid agglomeration of suspended particles.

As stated above, the dispersion in the present process is maintained primarily by mechanical agitation in a standard type mixing zone such as in a stirred reactor. However, maintenance of the suspension is enhanced and prolonged during polymerization by the addition of small amounts of suspension stabilizers of the type used to prevent agglomeration of the suspended droplets or globules which become more viscous and sticky as polymerization progresses. In effect, the stabilizer adheres to the surface of the globule and protects it from direct contact with another during the period when the polymeric globules are forming. The function of the stabilizer is particularly important in the present process where a high solids concentration is achieved.

Such stabilizers or suspension aids which are found to be useful in the suspension polymerization step are the poly-N-vinylpyrrolidone alkyl-modified polymers (e.g. N-vinyl-methylpyrrolidone polymers and copolymers with methyl substituted monomer) and the N-vinylpyrrolidone $C_{10}$ to $C_{20}$ olefin copolymers commercially available through GAF Corporation and marketed under the commercial names of ANTARON * P-904, ANTARON * P-804, ANTARON * V-816, GANEX * V-516, (preferred) GANEX * P-904, GANEX * V-220, GANEX * V-516, etc., which are substantially insoluble in the solvents of the present process. Generally, for the present purposes, the stabilizer is employed in an amount between about 0.5% and about 5% preferably between about 1% and about 3% by weight based on the weight of monomer. Conveniently, the above stabilizers are polymers having a number average molecular weight between about 8,000 and about 20,500.
*Trademark of GAF Corporation The catalyst or polymerization initiators found to be most effective in the suspension polymerization step are those of the free radical type which are soluble in the monomer. Accordingly, suitable initiators for the present process include azobisisobutyronitrile (commercially available as VAZO64), azobisisovaleronitrile (commercially available as VAZO52), dimethyl azodiisobutyrate, benzoyl peroxide, t-butyl hydroperoxide, t-butyl peracetate, acetyl peroxide, di-t-butyl peroxide, di-cumyl peroxide, cumyl hydroperoxide and generally any of the oil-soluble free radical initiators conventionally employed for polymerization. The particular initiator may be selected in accordance with the temperature of polymerization so that the catalyst remains in the liquid phase during reaction. In an oxygen free system, the proportion of initiator employed is between about 0.02% and 2% by weight, preferably between about 0.05% and about 1.0% by weight based on total weight of monomer. However, when oxygen contaminant is present, an additional amount of initiator is employed e.g. the above amount plus an equimolar amount for every mol of oxygen in a free state or reducible to a free state. Instead of, or in addition to, the initiators listed above, actinic light with or without the aid of a photosensitizer, e.g. benzophenone, fluorescein, eosin, etc., may be used but is less desirable.
** Trademark of duPont Corporation In general, the present suspension polymerization can be carried out by forming a mixture of the solvent, monomer, catalyst and suspension stabilizer. This mixture can be formed initially in the same zone or the mixture of monomer and solvent can be performed with or without the stabilizer and at least the initiator can be separately added thereto. Instead of this, a separate initiator mixture can be prepared and added to the monomeric suspension.

The molecular weights of the resultant PVP polymer produced thereby usually are about K-15 to about K-90 (10,000 to 360,000), which may be varied by kind and amount of catalyst used, and the temperature of the reaction. Higher molecular weights are obtained with a minimum amount of a given catalyst and lower temperatures, while lower molecular weights are obtained with increased amounts of catalyst and a higher temperature.

Alternatively, but less desirable, commercially available PVP powder of a given molecular weight may be used directly as a reactant for succeeding steps in the process. Accordingly, PVP K-30 powder may be suspended in a liquid, using a suitable suspending aid, and made available for the steps of addition of water and complexation with iodine, as described below. However, PVP prepared via suspension polymerization of VP generally requires less iodine to form the complex than with commercial material, probably due to particle size differences.

ADDITION OF WATER TO PVP SUSPENSION

Addition of water to the PVP suspension prior to complexation with iodine is necessary to form stable PVP iodine powders. Usually about 1-10% by weight of water is added to the PVP suspension, based on the PVP content, and preferably, about 5-8% by weight. The water may be added during the preceding polymerization step, but it is preferred to include it after polymerization has taken place, particularly if a lower molecular weight PVP polymer is desired.

Some water already may be present in the PVP itself, bound or otherwise, particularly in commercial material; however, this water usually is insufficient to provide the amount of water desired to form a stable complex.

COMPLEXATION OF PVP AND IODINE

Iodine is reacted with the in situ suspension of PVP containing the added water. Usually an elevated temperature is employed for this complexation step in order to reduce the time required for complete reaction. For rapid complex formation, a temperature above 65° C. is preferred; however, if the reaction temperature is too high, the complex will exhibit a loss of available iodine. Preferably a temperature between about 65° to 85° C. is used. A product having excellent stability properties may be prepared by heating at 75° C. for as short a time as 1-1½ hours.

Generally, the amount of iodine used is about 5-25%, preferably 10-20%, based on the weight of the PVP-iodine complex. However, the present process requires considerably less iodine (approximately 19% less) for processes than commercial which are made by dry milling of both reactants to prepare complex powder having an available iodine level of about 9.5-10%. Of course, if higher levels of available iodine are desired, then an increased iodine charge is employed. Similarly, if only a lower level of available iodine in the product is necessary, then a reduced charge of iodine is used. For any given available iodine level, however, the process of this invention requires less iodine than the commercial process mentioned.

RECOVERY OF PVP-IODINE COMPLEX

The solid PVP-iodine produced in the complexation step is recovered by filtration and, after dried the solid product is a pale yellow powder which is stable to washing with heptane even after prolonged storage. Later it may be made into a commercial solution by addition of a solvent therefor.

EXAMPLE 1

A 1 liter 4-necked cylindrical resin flask equipped with a stirrer, thermometer, dropping funnel and gas inlet tube is purged with nitrogen for about 15 minutes prior to charging. Then the following charge is added to the flask:

335 ml. (225 g.) of heptane
1.4 g. of Ganex V-516
55.5 g. vinylpyrrolidone
0.6 g. Vazo, and
55.5 g. vinylpyrrolidone is charged into the dropping funnel.

The funnel and flask are stoppered and a slight positive nitrogen pressure is maintained. The flask then is heated in a constant temperature bath to 75° C., whereupon a slight exotherm results, requiring cooling to 71° C. thereafter, addition of vinylpyrrolidone is begun drop-wise from the dropping funnel, and continued for 3 hours while maintaining the reaction temperature at about 71°–75° C., and thereafter for an additional 18 hours at 75° C.

To the polyvinylpyrrolidone suspension thus prepared is added 1.0 g. arlacel 85 (Atlas Chem.) — sorbitan trioleate — a surfactant dissolved in 5.0 ml. of heptane, and 8.8 g. of water (7.9% water based upon PVP content) is added dropwise over a period of 15 minutes.

The water-containing slurry then is stirred for ½ hour at 70°–72° C. and 18 g. of finely divided iodine is added incrementally over a period of ½ hour at 70°–75° C. The contents of the flask then are heated for an additional 2 hours at 75° C., cooled, filtered, and rinsed with heptane.

The product is dried in air overnight to give a yellow powder weighing 137 g. (99.7% yield), which is analyzed as follows:

Available iodine* = 9.93%
Water in powder = 5.3%
Available iodine (excluding water) = 10.48%
Loss in stability test** = 2.28%

*thiosulfate titration
**6 hours at 75° C.

EXAMPLE 2

The procedure of Example 1 is followed except that the polymerization is carried out by raising the temperature to 90°–95° C. after final addition of vinylpyrrolidone, followed by heating at this temperature for only 3 hours. The resultant solid complex product is otherwise the same as in Example 1.

EXAMPLE 3

The procedure of Example 1 is followed except that 5.5 g. to 8.8 g. of water (5.5 to 8.8% by weight water based on PVP) is added to the PVP suspension to provide a similar product.

EXAMPLE 4

The procedure of Example 1 is followed using hexane at 65° C. in place of heptane to provide a similar product.

EXAMPLE 5

To the apparatus of Example 1 is charged 100 g. of heptane and agitation is started while 0.5 g. Ganex V-516 is added followed by 50.0 g. polyvinylpyrrolidone K-30. The resultant slurry is stirred for ½ hour at ambient temperature, and then 2.5 g. of water is added dropwise with stirring for ½ hour. Then 10.0 g. of iodine is added as a fine powder over a period of 3/4 hour. After the addition is complete, the mixture is heated to 70° C. within 1 hour, and held at 70° C. for 3 hours. The contents then are cooled, filtered, rinsed, and dried. The solid complex product has properties similar to that prepared in Example 1.

Although the invention has been described with reference to certain embodiments thereof, it will be understood that changes and modifications may be made which are within the skill of the art. Accordingly, it is intended to be bound only by the following claims, in which;

What is claimed is:

1. An improved in situ process of forming a PVP-iodine complex powder which is stable for prolonged periods of time at a high level of iodine power, but which requires a reduced amount of iodine to form said complex at said level which comprises the following sequence of steps in combination:
   (a) suspension polymerizing vinylpyrrolidone in a solvent in which said vinylpyrrolidone is miscible but in which PVP is insoluble to form a slurry of polyvinylpyrrolidone powder in said solvent,
   (b) adding free water to said slurry in an amount of about 1–10% by weight of said polyvinylpyrrolidone thereby to form polyvinylpyrrolidone powder having a predetermined concentration of water therein, and,
   (c) adding finely divided elemental iodine to said slurry in an amount of about 5–25% by weight based on the complex at a temperature of about 65–85° C. and for a time sufficient to form said desired complex.

2. A process according to claim 1 wherein said water is added in an amount of about 5–8% by weight and said amount of iodine is about 10–20% by weight.

3. A process according to claim 2 wherein said reaction temperature is about 70°–75° C. and said reaction time is at least 1 1/2 hours.

4. A process according to claim 2 wherein said suspension polymerization is carried out in a saturated aliphatic hydrocarbon.

5. A process according to claim 4 wherein said saturated aliphatic hydrocarbon is selected from the group consisting of hexane and heptane.

* * * * *